United States Patent [19]

Slomski

[11] 3,971,143

[45] July 27, 1976

[54] DEVICE FOR TESTING THE ABILITY OF A PERSON TO RECOGNIZE SYNCHRONOUS SPEEDS

[76] Inventor: Waclaw Kazimierz Slomski, 426 Wilkinson St., Syracuse, N.Y. 13204

[22] Filed: Mar. 19, 1975

[21] Appl. No.: 557,661

[52] U.S. Cl. ............................................. 35/22 R
[51] Int. Cl.² ........................................ G09B 19/00
[58] Field of Search ............. 35/22 R, 11; 273/1 E

[56] References Cited
UNITED STATES PATENTS
3,641,686  2/1972  Krass............................... 35/22 R
FOREIGN PATENTS OR APPLICATIONS
136,800  2/1920  United Kingdom................. 35/22 R

*Primary Examiner*—William H. Grieb
*Attorney, Agent, or Firm*—Mason, Mason & Albright

[57] ABSTRACT

The equipment is to test psychologically drivers of all kinds of motor vehicles.

With this equipment one can test the competence in evaluating speed, which is based on the psychophysiological attribute, that is, the ability of perceiving motion.

Inside the casing, are located the electric system of the equipment and the driving mechanisms of the two disks. The left disk rotates with a constant rotational speed and has three constant rates of rotational speed. The right disk has three rates of variable speed, regulated automatically within certain limits by the tested person. The test consists in the tested person trying to regulate the rotation speed of the right disk in order to obtain the same rotation speed as on the left disk, within a specified period of time. The result of the test consists in measuring the differences in rotation speeds of both disks, as recorded automatically on the scale of the tachograph.

4 Claims, 3 Drawing Figures

DEVICE FOR TESTING THE ABILITY OF A PERSON TO RECOGNIZE SYNCHRONOUS SPEEDS

BACKGROUND OF THE INVENTION

The enormous development of street and highway traffic results in a steadily growing number of traffic accidents. These accidents bring about great material losses and, more importantly, are incommensurable in relation to human losses; loss of life, or permanent invalidism. The safety of traffic on the highways and streets depends to a considerable degree on the fact that a driver, to succeed in certain traffic situation must react in a proper way and sufficiently fast. The psychology of street and highway traffic tries to explain these problems. The subject of its investigation is a detailed analysis of the driver's work in order to establish psycho-physiological functions, indispensable for its safe execution. The driver's work has a specific character. In addition to some acquired information, training and possession of driving competence, the driver is also required to possess a particular psycho-physiological competence, considering the dynamics of the driver vehicle, and the human life and health hazards connected therewith.

Among the great number of drivers traveling on the streets and highways, there are some who often do not realize they have certain psycho-physiological deficiencies. This is why a necessity arises for controlling psycho-physiological characteristics of drivers before their licensing, and during their execution of work, as concerns changes, or disappearance of psycho-physiological competence.

The proper evaluation of psycho-physiological characteristics of a driver can be made only by using certain equipments, specialized and adapted for this aim. One such which so serves is my present invention. With the help of this equipment it will be possible to test the competence of evaluating speed, which is based on a psychical attribute, that is, the ability of perceiving motion.

The equipment of this invention together with other testing apparatus establishes methods of psychological tests for drivers of all kinds of motor vehicles. These tests have as an aim the reduction of the number of road and street traffic accidents which will contribute to the improvement of traffic safety on the roads.

DETAILED DESCRIPTION OF THE EQUIPMENT

Figure 2:
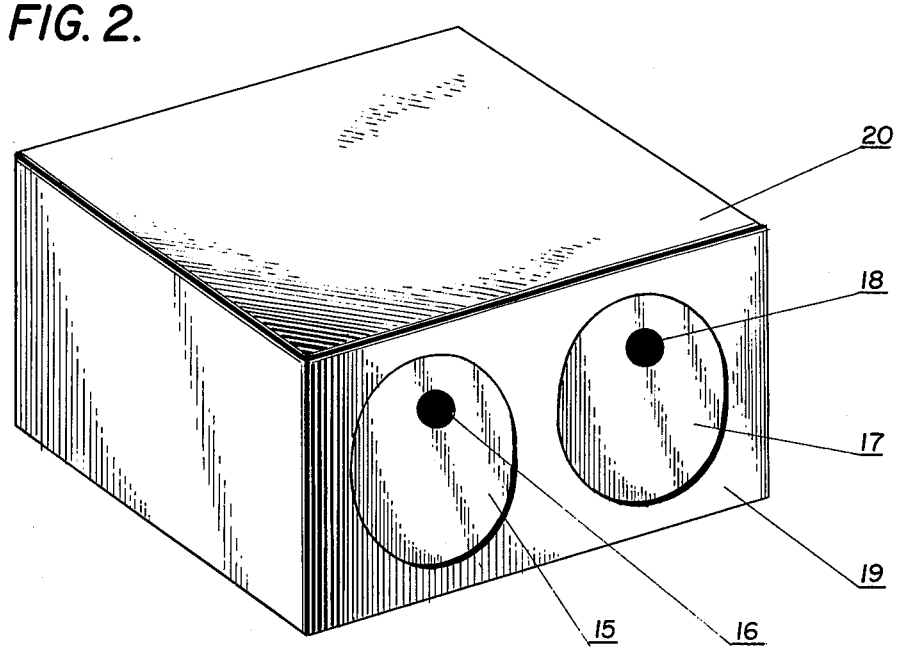

The invention comprises the feature of construction, combination of elements, and arrangement of parts, which will be exemplified in the construction hereinafter set forth, and the scope of the invention will be indicated in the claims.

The equipment has a wide application in testing people. It is primarily intended for psychological testing drivers of all kinds of motor vehicles, One can also test other people who work in certain specific conditions or for qualifying people for certain professions where there is a recognized need for competence of evaluating speed based on the psychical attribute, that is the ability of perceiving motion. The competence of evaluating speed combines the elements of perception, analysis and synthesis, as well as of understanding and of interpreting the phenomena observed. This is why, during the testing, it is required that the tested person possesses an efficient functioning of eyesight, an ability to concentrate attention, competence of comparing and evaluating the speed of objects in motion, and also the competence of rapidly making a decision.

The equipment is enclosed in a casing designated by reference numeral 20 in the following drawings.

Figure 1:
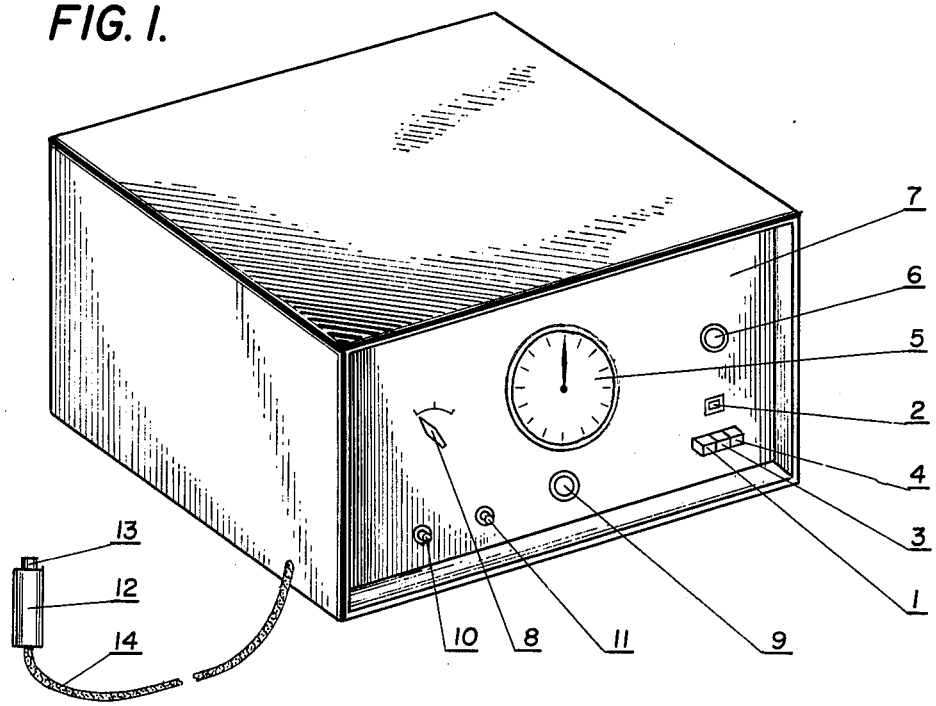

For a fuller understanding of the nature and objects of the invention, reference should be had to the following detailed description, taken in connection with the accompanying drawings, in which:

FIG. 1 presents a perspective view of the equipment, shown from the side of the testing person.

FIG. 2 presents a further perspective view of the equipment, shown from the side of the tested person.

Figure 3:
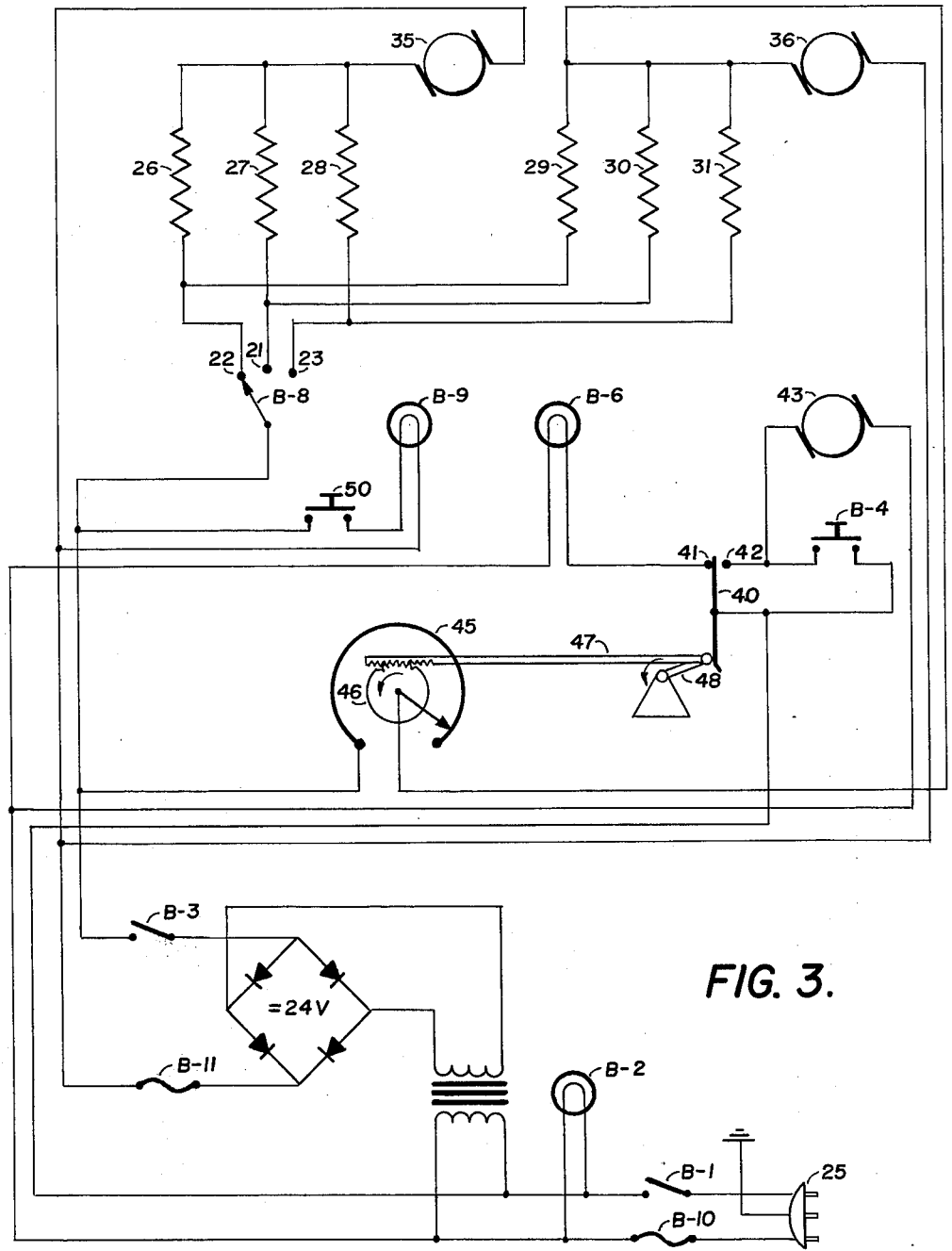

FIG. 3 presents the electric circuit diagram of the whole equipment.

FIG. 1 presents the switchboard 7, on which are located for control of the equipment, measuring-and-signalling, and protection of the equipment. The push-button switch 1 serves for connecting the equipment to the 115V supply network, which fact is signaled by the control lamp 2. The push-button switch 3 serves for connecting the 24V supply network of the equipment elements. The push-button 4 serves for switching on the automatic control of the right-side disk 17, FIG. 2. The tachometer 5 has a measuring range of rotation from zero to 700 rpm. The signal lamp 6 serves the testing person for indicating the beginning of the separate testing cycles. The knob 8 of the change-over switch serves for setting up the change-over switch for a given range of rotations of the motor driving the left-side disk 15, FIG. 2. The control lamp 9 signals the operation of the tested person, who reacts, by holding the clamp 12 by pressing on the push-button 13. The clamp 12 to the push-button 13 is connected by a conductor with the electric supply system of the equipment. The fuse 10 serves to protect the 115V network, and the fuse 11 serves to protect the 24V network.

FIG. 2 presents in perspective the equipment from the side of the tested person. On the side wall 19 of the casing 20 two round rotary disks are visible, the left disk 15 and the right disk 17. The disks are painted white. At a specified distance from the center of discs rotation circles 16 and 18 are painted in black. The dimensions of both disks 15 and 17 are identical, as well as the location and size of the black circles 16 and 18 on these disks. The left-side disk 15 has three fixed speed ranges. The right-side disk 17 has three variable speeds, where its rise and decline of rotations is automatically regulated during a preset time.

METHOD OF CONDUCTING TESTS

The equipment is placed in front of the tested person in such a way that the disks 15 and 17, FIG. 2, are at a distance of 3m from the eyes of the tested person.

The left-side disk 15, FIG. 2, has three fixed rotation speed ranges, 200, 400 and 600 rpm. The right-side disk 17, FIG. 2, has three ranges of variable rotation speeds. On the first speed range the disk rotation speed is automatically controlled during a preset time, when a rise from 100 rpm to 300 rpm occurs, and then back a fall from 300 rpm to 100 rpm. In the second speed range the disk rotation speed is automatically regulated during a preset time, when a rise from 300 rpm to 500 rpm occurs, and then back a fall from 500 rpm to 300 rpm. In the third speed range the disk rotation speed is automatically regulated during a preset time, when a rise from 500 rpm to 700 rpm occurs, and then back a fall from 700 rpm to 500 rpm.

During the test the task of the tested person consists in reacting by pressing push-button 13, FIG. 1, at the moment, when the revolutions of the right-side disk 17, FIG. 2, during their rising or falling, will equal the fixed rate of revolutions of the left-side disk 15, FIG. 2. For example, the left-side disk 15, FIG. 2, rotates with a fixed speed of 200 rpm, while the right-side disk 17, FIG. 2, starts rotating with an initial speed of 100 rpm. After the pressing of the push-button switch 4, FIG. 1, the mechanism for automatically accelerating the rotation speed of the right-side disk 17, FIG. 2, is switched on, and during a specified time accelerates steadily the rotation speed of the disk 17, FIG. 2, up to 300 rpm, and then reduces the rotation speed also automatically and steadily from 300 rpm to 100 rpm. During the rpm acceleration period the tested person ought to press the push-button 13, FIG. 1, at the moment when the rotations of the right-side disk 17, FIG. 2, will equal the rotation speed of the left-side disk 15, FIG. 2, i.e., 200 rpm. After the rotation speed of the right-side disk 17, FIG. 2, reaches 300 rpm, the rotation speed of this disk automatically starts to decelerate to 100 rpm. During the fall of the rotation speed of the disk 17, FIG. 2, the tested person ought to press again the push-button 13, FIG. 1, at the moment when the speed of rotation of the right-side disk 17, FIG. 2, will equal 200 rpm. At the moment of pressing the push-button 13, FIG. 1, the signal lamp 9, FIG. 1, lights up and the testing person reads the result of the test on the recording scale of the tachometer 5, FIG. 1, which indicates the variable rotations of the right-side disk 17, FIG. 2. In the same way tests are carried on at the ranges of speeds 400 rpm and 600 rpm.

The result of these tests are the deviations of rotation speeds of the right-side disk 17, FIG. 2, in relation to the rotation speeds of the left-side disk 15, FIG. 2, measured at every one of the three fixed ranges of rotation speeds at the ascending and descending cycles. The evaluation of the results of the test is made on the basis of an average percentage deviations measured for the three ranges of fixed rotation speeds.

FIG. 3 presents the electric connections diagram of the whole equipment. The equipment is supplied from the 115-V/60 Hz electric network. After connecting the plug 25 into the socket of the 115-V network and switching-on the push-button switch B-1, the B-2 signal lamp and the 24-V rectifier are switched on. The fuse B-10 protects the 115-V supply network, and the fuse B-11 protects the 24-V supply network. After the switching-on the B-3 switch, the equipment is ready for carrying-on the tests. Then the current flows to the change-over switch B-8 across the contacts 22 and resistor 26 to the driving motor 35 of the leftside disk 15, FIG. 2. With the placement of the change-over switch B-8 in the position 22, and with the switching-on of the resistor 26, the motor 35 drives the left-side disk 15, FIG. 2, with the fixed rotating speed of 200 rpm. With the placement of the change-over switch B-8 in the position 22, the current flows simultaneously across the resistor 29 to the driving motor 36 of the right-side disk 17, FIG. 2, which drives this disk with the rotating speed of 100 rpm. With the placing of the changeover switch B-8 in the position 21, and with the switching-on the resistor 27, the motor 35 drives the left-side disk 15, FIG. 2, with the fixed rotating speed of 400 rpm. With the placing of the change-over switch B-8 in the position 21, the current will flow simultaneously across the resistor 30 to the motor 36 of the right-side disk 17, FIG. 2, which drives this disk with the rotating speed of 300 rpm. With the placing of the change-over switch in the position 23, and with the switching-on the resistor 28, the motor 35 drives the left-side disk 15, FIG. 2, with the fixed rotating speed of 600 rpm. With the placing of the change-over switch B-8 in the position 23, the current will flow simultaneously across the resistor 31 to the electric motor 36, which drives the right-side disk 17, FIG. 2 with the rotating speed of 500 rpm.

A special mechanism, driven by the electric motor 43, serves for accelerating and for retarding the rotating speed of the motor drive 36 of the right-side disk 17, FIG. 2. The motor drive 43 is equipped with a transmission, which rotates a connecting rod 48.

The toothed rack 47 is fixed on the connecting rod 48; this rack with its translational-sliding-and-reversible motion, rotates the gear-wheel 46. One turn of the connecting rod 48 causes the turn of the gear-wheel 46 to the left, and back to the right, in the range of 300°. The brush of the adjustable resistor 45 is fastened to the axis of the gearwheel 46. This brush, during its turn to the left, sliding on the resistor 45, causes the increase of rotations of the right-side disk, FIG. 2. The terminal position of the brush during the turn to the left, and with the appropriate arrangement of the change-over switch B-8, causes the increase of the speed of rotation of the right-side disk 17, FIG. 2, from 100 to 300 rpm, from 300 to 500 rpm, and from 500 to 700 rpm. With the return turn of the brush to the right side, to the initial position, the rotation speeds decline accordingly, depending on the arrangement of the change-over switch B-8 for rotations 100, 300, and 500 rpm. The electric drive 43 secures only one turn of the connecting rod 48, which turning around its axis, in the terminal position presses on the end of the spring 40, and disconnects the contact 42. At this time, the electric drive 43 is stopped. At this moment, the testing at the given rotation speed of the left-side disk 15, FIG. 2, is terminated; this is signalized by the control lamp B-6, which is switched-on by the contact 41. After the placement of the change-over switch B-8, and switching-on in turn the following rotation speed of the left-side disk 15, FIG. 2, one presses the push-button switch B-4, which operates the electric drive 43 of the acceleration and deceleration of the speed of rotation of the motor 36, which drives the right-side disk 17, FIG. 2. The signal lamp B-9 is lighted up by the tested person by pressing the push-button 50. The tested person ought to press the push-button 50 at the moment, when the rotation speed of the right-side disk 17, FIG. 2, will be equal to the rotation speed of the left-side disk 15, FIG. 2.

By analyzing the results, obtained during the tests, one will be able to evaluate the given person as to the degree of the given psycho-physiological feature possessed, and thereby to foresee good or bad results of performing the task for which this person was tested.

The above described equipment has been built as a model. All its electric and mechanical systems operate accurately, and meet perfectly the requirements. The equipment can unreservedly be used for psychological tests.

Having described my invention, what I claim as new, and desire to secure by Letters Patent, is:

1. Apparatus for testing the capacity of perceiving motion which comprises a pair of rotatable discs with identical indicia applied thereto, said discs being located where they can be viewed simultaneously by a person being tested, separate electric motors each driving a separate said disc, electric circuit means supplying electric current to each said motor, one of said discs being driven by its corresponding electric motor at a predetermined constant rotational speed, automatic control means continually changing the rotational speed of the other of said discs in a predetermined manner whereby the rotational speed of said other disc varies within a range from lower than that of the one said disc to higher than that of the one said disc, rotational speed indication means indicating the rotational speed of said other disc, and selector means for the person being tested to signal when in his judgment the rotational speeds of said pair of discs are the same.

2. Apparatus for testing the capacity of perceiving motion in accordance with claim 1 wherein the rotational speed of each motor is determined by resistance elements in said electric circuit means to each said motor.

3. Apparatus for testing the capacity of perceiving motion in accordance with claim 2 wherein said automatic control means comprises a variable resistance component in said circuit means for said motor driving said other disc and adjustment means for varying the resistance of said variable resistance component in a predetermined manner.

4. Apparatus for testing the capacity of perceiving motion in accordance with claim 3 wherein said adjustment means comprises an electric motor which is energized by said circuit means.

* * * * *